(12) United States Patent
Kruit et al.

(10) Patent No.: US 8,895,921 B2
(45) Date of Patent: Nov. 25, 2014

(54) INSPECTION APPARATUS AND REPLACEABLE DOOR FOR A VACUUM CHAMBER OF SUCH AN INSPECTION APPARATUS AND A METHOD FOR OPERATING AN INSPECTION APPARATUS

(75) Inventors: Pieter Kruit, Delft (NL); Jacob Pieter Hoogenboom, De Meern (NL); Aernout Christiaan Zonnevylle, Dordrecht (NL)

(73) Assignee: Delmic B.V., JD Delft (NL)

( * ) Notice: Subject to any disclaimer, the term of this patent is extended or adjusted under 35 U.S.C. 154(b) by 0 days.

(21) Appl. No.: 13/809,685

(22) PCT Filed: Jul. 14, 2011

(86) PCT No.: PCT/NL2011/050513
§ 371 (c)(1),
(2), (4) Date: Apr. 29, 2013

(87) PCT Pub. No.: WO2012/008836
PCT Pub. Date: Jan. 19, 2012

(65) Prior Publication Data
US 2013/0200262 A1 Aug. 8, 2013

(30) Foreign Application Priority Data
Jul. 14, 2010 (NL) ..................................... 2005080

(51) Int. Cl.
*H01J 37/26* (2006.01)
*G01N 21/62* (2006.01)
*H01J 37/22* (2006.01)
*H01J 37/256* (2006.01)
*H01J 37/28* (2006.01)

(52) U.S. Cl.
CPC ......... *H01J 37/22* (2013.01); *H01J 2237/2445* (2013.01); *H01J 37/26* (2013.01); *H01J 37/228* (2013.01); *H01J 2237/2482* (2013.01); *H01J 37/256* (2013.01); *H01J 2237/204* (2013.01); *H01J 37/28* (2013.01); *G01N 2021/625* (2013.01); *H01J 2237/2808* (2013.01); *H01J 37/226* (2013.01); *G01N 21/62* (2013.01)

USPC ........... 250/306; 250/307; 250/309; 250/310; 250/311; 250/458.1; 356/317

(58) Field of Classification Search
CPC ................ H01J 2237/082; H01J 37/20; H01J 2237/2482; H01J 37/226; H01J 2237/31745; H01J 37/228; H01J 37/26
USPC .............. 250/306, 307, 309, 310, 311, 458.1; 356/317
See application file for complete search history.

(56) References Cited

U.S. PATENT DOCUMENTS 6,259,104 B1    7/2001  Baer
(Continued)

FOREIGN PATENT DOCUMENTS

DE            3904280 A1    8/1990
(Continued)

OTHER PUBLICATIONS

International Search Report dated Jan. 18, 2012 for Application No. PCT/NL2011/050513.
Patent Abstracts of Japan English abstract of JP 56-27640 A, Mar. 1981.
espacenet English abstract of DE 3904280 A1, Aug. 1990.
(Continued)

*Primary Examiner* — Nikita Wells
(74) *Attorney, Agent, or Firm* — Ladas & Parry LLP

(57) ABSTRACT

An inspection apparatus is provided comprising in combination at least an optical microscope (2, 3, 4) and an ion- or electron microscope (7, 8) equipped with a source (7) for emitting a primary beam (9) of radiation to a sample (10) in a sample holder. The apparatus may comprise a detector (8) for detection of secondary radiation (11) backscattered from the sample and induced by the primary beam. The optical microscope is equipped with an light collecting device (2) to receive in use luminescence light (12) emitted by the sample and to focus it on a photon-detector (4).

17 Claims, 6 Drawing Sheets

(56) References Cited

U.S. PATENT DOCUMENTS

| | | | | |
|---|---|---|---|---|
| 7,626,694 | B2* | 12/2009 | Betzig et al. | 356/317 |
| 7,782,457 | B2* | 8/2010 | Betzig et al. | 356/317 |
| 8,481,980 | B2* | 7/2013 | Shichi et al. | 250/492.21 |
| 2003/0053048 | A1 | 3/2003 | Bennett et al. | |
| 2004/0090621 | A1 | 5/2004 | Bennett et al. | |
| 2006/0098188 | A1 | 5/2006 | Buijsse et al. | |

FOREIGN PATENT DOCUMENTS

| | | |
|---|---|---|
| DE | 10 2009 015 341 A1 | 7/2010 |
| EP | 1 087 610 A2 | 3/2001 |
| EP | 1 956 633 A2 | 8/2008 |
| JP | 56-27640 A | 3/1981 |
| WO | 01/27967 A1 | 4/2001 |

OTHER PUBLICATIONS

Wouters, C.H., et al., "Specimen stage incorporating light microscopical optics for a Cambridge S180 scanning electron microscope", Journal of Microscopy, vol. 145, Pt 2, Feb. 1987, pp. 237-241.

Toledo-Crow, R., et al., "Contrast mechanisms and imaging modes in near field optical microscopy", Ultramicroscopy, vol. 57, No. 2-3, (Feb. 1995), pp. 293-297.

Pavier, M.A., et al., "Electroluminescence from dysprosium- and neodymium-containing LB films", Thin Solid Films 284-285, (Sep. 1996), pp. 644-647.

Degraff, B.A., et al., "Vibrational Spectroscopy: an Integrated Experiment", The Chemical Educator, vol. 1, No. 6, 1996, pp. 1-21.

Office Action dated Jul. 11, 2014 in connection with Application No. EP 11 748 478.2-1556.

espacenet English abstract of DE 10 2009 015 341 A1.

* cited by examiner

INSPECTION APPARATUS AND REPLACEABLE DOOR FOR A VACUUM CHAMBER OF SUCH AN INSPECTION APPARATUS AND A METHOD FOR OPERATING AN INSPECTION APPARATUS

RELATED APPLICATION INFORMATION

This application is a 371 of International Application PCT/NL2011/050513 filed 14 Jul. 2011 entitled "Inspection Apparatus And Replaceable Door For A Vacuum Chamber Of Such An Inspection Apparatus And A Method For Operating An Inspection Apparatus", which was published in the English language on 19 Jan. 2012, with International Publication Number WO 2012/008836 A2, and which claims priority from NL Patent Application No. 2005080 filed on 14 Jul. 2010, the content of which is incorporated herein by reference.

The invention relates to an inspection apparatus comprising in combination at least an optical microscope and an ion- or electron microscope equipped with a source for emitting a primary beam of radiation to a sample in a sample holder, wherein the optical microscope is equipped with a light collecting device to receive in use luminescence light emitted by the sample and to focus it on a photon-detector. The invention also relates to a replaceable door for a vacuum chamber of such an inspection apparatus. The invention also relates to a method of operating an inspection apparatus comprising in combination at least an optical microscope and an ion- or electron microscope.

Such an inspection apparatus is known from the article Specimen stage incorporating light microscopical optics for a Cambridge 5180 scanning ion- or electron microscope by C. H. Wouters et al, Journal of Microscopy, volume 145, part two, February 1987, pages 237-240. In this known inspection apparatus the optical microscope is at least in part placed externally of the vacuum chamber of an electron microscope.

The known inspection apparatus provides the possibility to merge images from the sample derived from both the electron microscope and the optical microscope. It is however a problem to properly relate the images from both microscopes due to their huge difference in resolution. An ion- or electron microscope may provide images with a resolution in the range of 1 nm, whereas the resolution of the optical microscope is in the range of 300-500 nm. It is an object of the invention to provide and to operate an inspection apparatus in order to obtain an improved resolution in all applicable measurement directions.

According to the invention an inspection apparatus and a replaceable door for a vacuum chamber of an ion- or electron microscope is proposed in accordance with one or more of the appended claims.

The primary beam may be provided by the ion- or electron microscope and may be an ion or an electron beam. The ion- or electron microscope may be a scanning ion- or electron microscope. The ion- or electron microscope may comprise a detector arranged for the detection of secondary electron and/or for the detection of radiation, emitted, transmitted or scattered from the sample and possibly induced by the primary beam. The scattered radiation may be back-scattered radiation. However, in some embodiments this detector may be omitted.

In an embodiment of the invention the optical microscope is of the confocal type having a pinhole between the light collecting device and the photon-detector. This provides improved resolution in the x and y direction of the sample in the range of 1 nm, whereas the pinhole secures resolution in the z direction of the sample in the range of 300 or 500 nm.

In an optical microscope wherein luminescence light is excited with a light beam, the resolution in the lateral, or x- and y-directions may be in the range of 300 nm. In a cathodoluminescence microscope, the resolution in the lateral directions may be in the range of 1 nm. However, in that case, using a primary beam, the resolution in the z direction, which is perpendicular to both x and y directions, may be in the range of 5 micrometers.

In the inspection apparatus according to an embodiment of the invention, the use of a pinhole may provide a improved resolution in the z-direction of the sample in the range of 500 nm. In that case, the resolution of both the techniques may be in the same order.

The light collecting device (which can also be plural devices) can advantageously be selected from the group comprising an objective, a mirror, a glass fiber. In this application the use of an objective will be further used for the elucidation of the invention, however it is likewise possible to apply a mirror or a glass fiber or any other suitable means or combinations thereof.

In another aspect of the invention the inspection apparatus is embodied with a light source and ancillary means for directing light to the sample and excite it to emit luminescence light and to enable its detection by the optical microscope. These ancillary means for directing the light to the sample may comprise mirror(s), dichroic mirror(s), filters, Nipkov spinning disk, spatial light modulator(s), deformable mirror(s), polarizer(s) and/or beam splitter(s).

In general, luminescence light may be fluorescence light, but it may also be cathodoluminescence light. In latter case the sample may be excited by the primary beam.

This embodiment provides the opportunity to investigate a modification of the luminescence light induced by the light source, where the modification may be induced by the primary beam, and the luminescence light which is induced by the primary beam of radiation of the ion- or electron microscope. In the latter case, a modification of the luminescence light may be induced by the light source. The measured modulation in the luminescence light allows for improving the resolution of the image that is derived from the sample that is based on the light source.

Furthermore, superresolution may be achieved, when the sample is illuminated by the light source (for example a laser beam) with a light spot and scanned with the primary beam within the light spot on the sample. The photon detector may detect the luminescence light emitted by one or more emitting elements (which may comprise one or more markers), located in the sample and exposed to the exciting light. Typically multiple emitting elements are located within the light spot. When the primary beam hits a marker, the resulting luminescence light may change, for example its intensity, its wavelength spectrum and/or its time-delay with respect to the illumination with the light.

Coincidence of the instantaneous position of the primary beam with the instant of change in the resulting luminescence light allows the retrieval of the position of this one marker.

In an embodiment, the apparatus comprises source ancillary means, wherein the source and said source ancillary means are arranged for emitting and directing said primary beam (9) with a beam intensity to a beam position on said sample during a continuous beam exposure period, and preferably for varying the beam intensity during the beam exposure period. These ancillary means for directing said primary beam may comprise electromagnetic lenses, deflectors, multipoles and/or apertures. The beam intensity may be expressed as the current of the beam at the sample, the kinetic energy of the particles in the beam or a combination of both.

It may be the case that the photon-detector is arranged for detecting the luminescence light emitted by the sample during said beam exposure period.

The primary beam may influence the excitation of and the emission of luminescence light by the sample or elements of the sample, for example markers, depending on the beam intensity. The sample may comprise different markers which are influenced differently by the primary beam at a certain beam intensity. By varying the beam intensity those different markers may be detected.

In a further embodiment, the source and the source ancillary means are arranged for varying the beam intensity during the beam exposure period with a predefined frequency. The variation of the beam intensity with a predefined frequency may cause that the intensity of the luminescence light also exhibits a variation with the same frequency. This may be used to filter the light received by the photon-detector, for example by using a so called lock-in detection method. It may also be used to study characteristics of the marker, such as the life-time of an excited state of the marker.

In an embodiment the light source and ancillary means are arranged for directing light with a light intensity to a light position on said sample during a continuous light exposure period and preferably for varying the light intensity during the light exposure period. In a further embodiment, the light source and ancillary means are arranged for varying the light intensity during the light exposure period with a further predefined frequency.

It may be the case that the photon-detector is arranged for detecting the luminescence light emitted by the sample during said light exposure period.

The light may influence the excitation of and the emission of luminescence light by (elements of) the sample depending on the light intensity. The light intensity may be expressed as the amount of photons per unit of time in the light beam, or the amount of energy per unit time in the light spot at the sample or at the detector, or a combination of both. The sample may comprise different elements which are influenced differently by the light at a certain light intensity. By varying the light intensity those different elements in may be detected. The variation of the light intensity with a predefined frequency may cause that the intensity of the luminescence light also exhibits a variation with the same frequency. This may be used to filter the light received by the photon-detector or to study characteristics of (elements of) the sample.

A spot size of the light on the sample may be much larger than a spot size of the primary beam on the sample and the beam exposure period may be much shorter than the light exposure period. Indeed, during the light exposure period, the spot of the light on the sample may be scanned with the primary beam.

In an embodiment of the invention, the inspection apparatus further comprises a processing unit, which may be arranged for determining a characteristic of an element of the sample. An example of a characteristic of an element of the sample may be a life time of excited state of said element. This life time may be with respect to the excitation by the light or by the primary beam. On the basis of a determined life time, a marker may be identified.

In an embodiment of the invention, said processing unit is arranged for determining variations, during the light exposure period or the beam exposure period, of at least one of: a light intensity of the received luminescence light, a wavelength spectrum of the received luminescence light, wave vector of the received luminescence light, the life time of an excited state, and a polarisation of the received luminescence light. In a further embodiment, the processing unit is arranged for determining a characteristic of an element of the sample based on at least one determined variation.

Variation of the light intensity, the wavelength spectrum, wave vector of the received luminescence light, the life time of an excited state, and/or the polarisation of the received luminescence light may provide information about the element and may enable identification of the element, for example the marker.

In an embodiment of the invention, the processing unit is arranged for determining variations, during the light exposure period or the beam exposure period, of at least one of: detected secondary radiation and detected radiation, emitted, transmitted or scattered from the sample and possibly induced by the primary beam. In a further embodiment, the processing unit is arranged for determining a characteristic of an element of the sample based on at least one determined variation.

Also these variations may provide information about the element and may enable identification of the element In an embodiment, the optical microscope is provided with another pinhole between the light collecting device and the photon-detector and next to the pinhole.

The photon-detector may be arranged to detect two light beams from the sample, wherein the two light beams may be generated by different processes (such as reflection, fluorescence and cathodoluminescence), and/or may be from different locations in the sample. It may be advantageous to detect both light beams at same time by two separate confocal detectors. However, the two confocal detectors may share one photon-detector, such as a CCD camera, while having two different pinholes, one pinhole for each light beam. Likewise, the microscope may comprise more than two pinholes.

In an embodiment of the invention, the source and the source ancillary means are arranged for emitting and directing said primary beam to a beam position on said sample during a continuous beam exposure period and for emitting said primary beam to another beam position on said sample during another continuous beam exposure period after the beam exposure period,
wherein the other beam position is located randomly with respect to the beam position; and/or wherein the other beam position and the beam position are part of a predefined area of interest on said sample.

In an embodiment of the invention, the light source and ancillary means are arranged for directing light to another light position on said sample during another continuous light exposure period after the continuous light exposure period, wherein the other light position is located randomly with respect to the light position; and/or wherein the other light position and the light position are part of a predefined area of interest on said sample.

During the scanning with the primary beam, the position of the light beam should more or less constant in order to determine the position of one or more markers. However, it may be impossible to prevent unintended variations of the position of the light beam. These unintended variations may be caused by temperature variation or vibrations. When scanning the sample line by line, these variations may cause errors in the determination of the position of elements or markers in the sample.

An advantage of scanning the sample randomly by the primary beam or the light may be that these errors may also be random and may thus be corrected for.

It may be the case that the sample comprises areas of interest. These areas may have been identified after studying the whole sample using reflection microscopy, transmission microscopy and/or luminescence microscopy. It may be advantageous to scan only these area with the primary beam and/or light.

A further preferable embodiment of the inspection apparatus of the invention has the feature that the primary beam of radiation is directed to the sample at an acute angle with respect to the optical axis of the light collecting device. In this way it is possible to further restrict the volume area of the sample from which the cathodoluminescence light is collected and thus further improve resolution.

A still further preferable embodiment of the inspection apparatus of the invention is characterized in that it has two primary beams that are directed at equal angles of opposite sign to the sample. It may have more than two, for example three, primary beams that are directed at equal angels with respect to the optical axis.

This provides the possibility that a stereo image can be recorded which can be used to improve the resolution even still further. Intensities of both the primary beams can then be tuned in a way that only signals originating from the area where both beams overlap are recorded.

Generally speaking an inspection apparatus comprising an ion- or electron microscope has a vacuum chamber that is provided with a door. In still a further aspect of the invention on the door is mounted one or more selected from the group comprising the sample holder, the optical microscope or a part thereof, the light source and its ancillary means for directing light to the sample. This allows for retrofitting an existing inspection apparatus of the prior art into an inspection apparatus of the invention by simply replacing its door. The replacing door then only has to be provided with one or more selected from the group comprising a sample holder for a sample to be investigated, an optical microscope of the confocal type or a part thereof, a light source with ancillary means for directing light to a sample to be placed in the sample holder and the processing unit.

The object of the invention is also met by providing a method operating an inspection apparatus comprising in combination at least an optical microscope and an ion- or electron microscope, comprising the steps of:

emitting, and preferably directing, a primary beam of radiation to a sample in a sample holder; and, receiving the luminescence light emitted by the sample.

In an embodiment according to the invention, the method further comprises:

directing light from a light source to the sample in order to excite it to emit luminescence light.

In an embodiment according to the invention, the luminescence light emitted by the sample is induced by the primary beam of radiation and/or by the light from the light source. In an embodiment according to the invention, the primary beam of radiation and the light originating from the light source illuminate the sample simultaneously or with a preselected time-delay.

In an embodiment according to the invention, the method further comprises the step of:

detecting a secondary radiation backscattered from the sample and induced by the primary beam or radiation, emitted, transmitted or scattered from the sample and possibly induced by the primary beam.

In an embodiment according to the invention, the optical microscope is of the confocal type having a pinhole between the light collecting device and the photon-detector.

In an embodiment according to the invention, said primary beam is emitted, and preferably directed, with a beam intensity to a beam position on said sample during a continuous beam exposure period.

In an embodiment according to the invention, the method further comprises the step of: varying the beam intensity during the beam exposure period, preferably with a predefined frequency.

In an embodiment according to the invention, said light is directed with a light intensity to a light position on said sample during a continuous light exposure period.

In an embodiment according to the invention, the method further comprises the step of: varying the light intensity during the light exposure period, preferably with a further predefined frequency.

In an embodiment according to the invention, the method further comprises the step of:

determining variations, during the light exposure period or the beam exposure period, of at least one of: a light intensity of the received luminescence light, a wavelength spectrum of the received luminescence light, wave vector of the received luminescence light, a life time of an exited state, and a polarisation of the received luminescence light.

In an embodiment according to the invention, the method further comprises the step of:

determining variations, during the light exposure period or the beam exposure period, of at least one of: detected secondary radiation and detected radiation, emitted, transmitted or scattered from the sample and possibly induced by the primary beam.

In an embodiment according to the invention, the method further comprises the step of:

determining a characteristic of an element of the sample, such as a life time of an excited state of the element, preferably based on at least on of the determined variations.

In an embodiment according to the invention, the ion- or electron microscope is of the confocal type.

In an embodiment according to the invention, the method comprises the step of:

emitting and directing the primary beam (9) to another beam position on said sample after the beam exposure period during another continuous beam exposure period, wherein the other beam position is located randomly with respect to the beam positions; and/or, wherein the other beam position and the beam position are part of a predefined area of interest on said sample.

In an embodiment according to the invention, the method further comprises the step of:

directing the light to another light position on said sample after the light exposure period during another continuous light exposure period, wherein the other light position is located randomly with respect to the light position; and/or, wherein the other light position and the light position are part of a predefined area of interest on said sample.

In an embodiment according to the invention, the method further comprises the step of:

emitting and directing the primary beam (9) to another beam position on said sample after the beam exposure period during another continuous beam exposure period; and, directing the light to another light position on said sample after the light exposure period during another continuous light exposure period;

wherein both said steps take place at the same time, with another time-delay or independently from each other.

The effects and the advantages of the embodiments of the method may be similar to the effect and the advantages of the embodiments of the inspection apparatus as described above.

The invention will hereinafter be further elucidated with reference to several exemplary embodiments of an inspection apparatus according to the invention, as shown in the drawing.

In the drawing.

Wherever in the figures the same reference numerals are applied, these numerals relate to the same parts.

Figure 1:
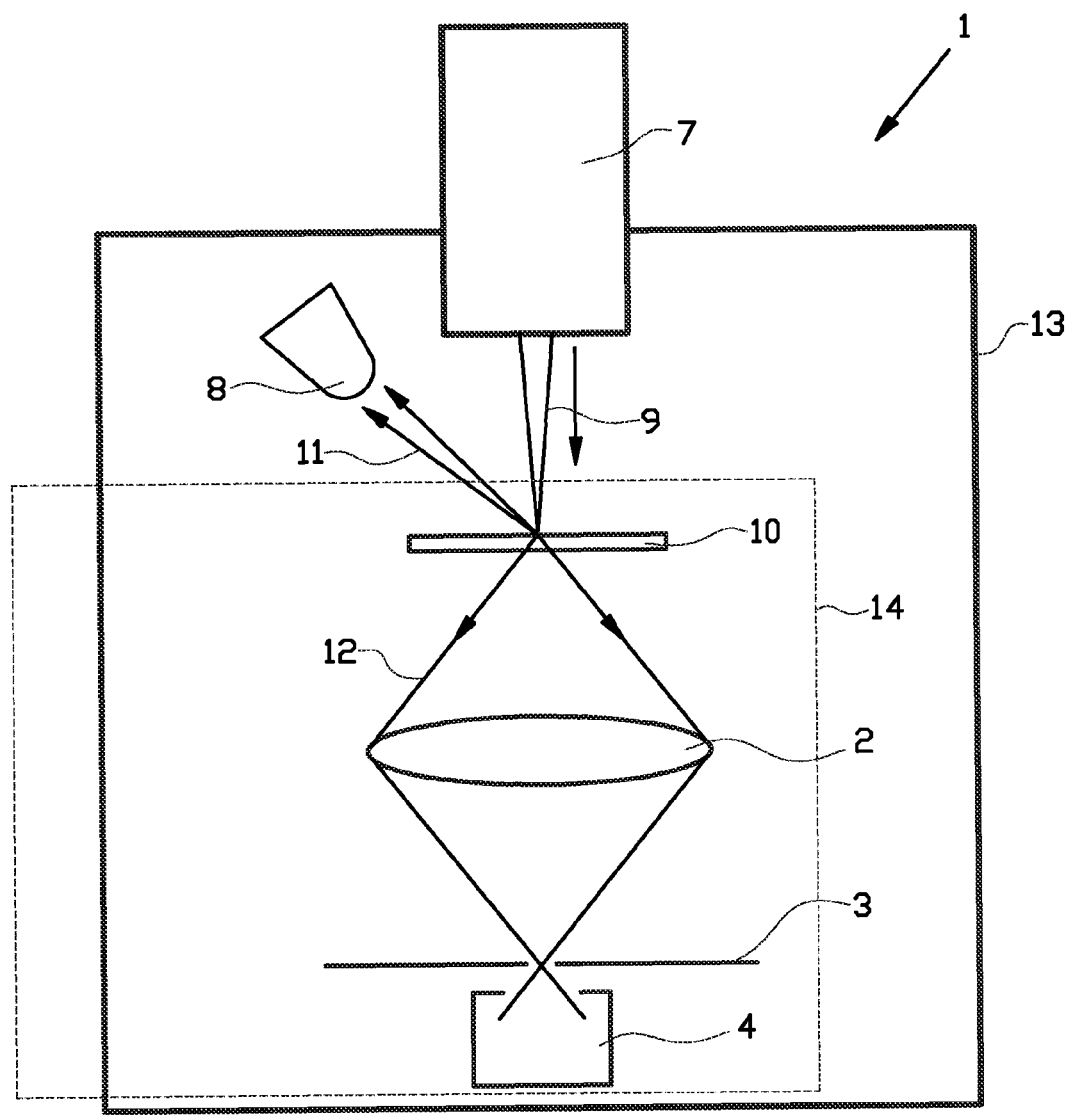
FIG. 1 shows schematically a basic design of an inspection apparatus of the invention.

With reference first to FIG. 1 the basic design of the inspection apparatus 1 of the invention can be explained. This inspection apparatus 1 comprises in combination at least an optical microscope 2, 3, 4 and an ion- or electron microscope 7, 8 equipped with a source 7 for emitting a primary beam 9 of radiation to a sample 10 in a sample holder. The apparatus may comprise a detector 8 for detection of secondary radiation 11 backscattered from the sample 10, or emitted, transmitted, or scattered from the sample 10 and possibly induced by the primary beam 9. The optical microscope 2, 3, 4 is equipped with an light collecting device 2 to receive in use luminescence light 12 emitted by the sample 10 and induced by the primary beam 9 of radiation and to focus it on a photon-detector 4. The light collecting device 2 may be an objective, a mirror or a glass fiber. It may also consist of a plurality of devices to arrange for collecting and focusing of the concerning luminescence light that is emitted by the sample 10. In the following discussion use will be made of an objective 2 as light collecting device.

The optical microscope 2, 3, 4 is of the confocal type having a pinhole 3 between the objective 2 and the photon-detector 4. In this embodiment of FIG. 1 the optical microscope 2, 3, 4 is placed entirely inside the vacuum chamber 13 of the ion- or electron microscope 7, 8. The closed dashed line 14 encircles those parts of the inspection apparatus 1 of the invention that may all or some of them be mounted on the (replaceable) door of the vacuum chamber 13, notably the sample holder for the sample 10, the light collecting device 2, the pinhole 3, and the photon-detector 4. This construction enables an easy retrofit or completion of an existing ion- or electron microscope according to prior art in order to convert it into an inspection apparatus according to the invention.

Figure 2:
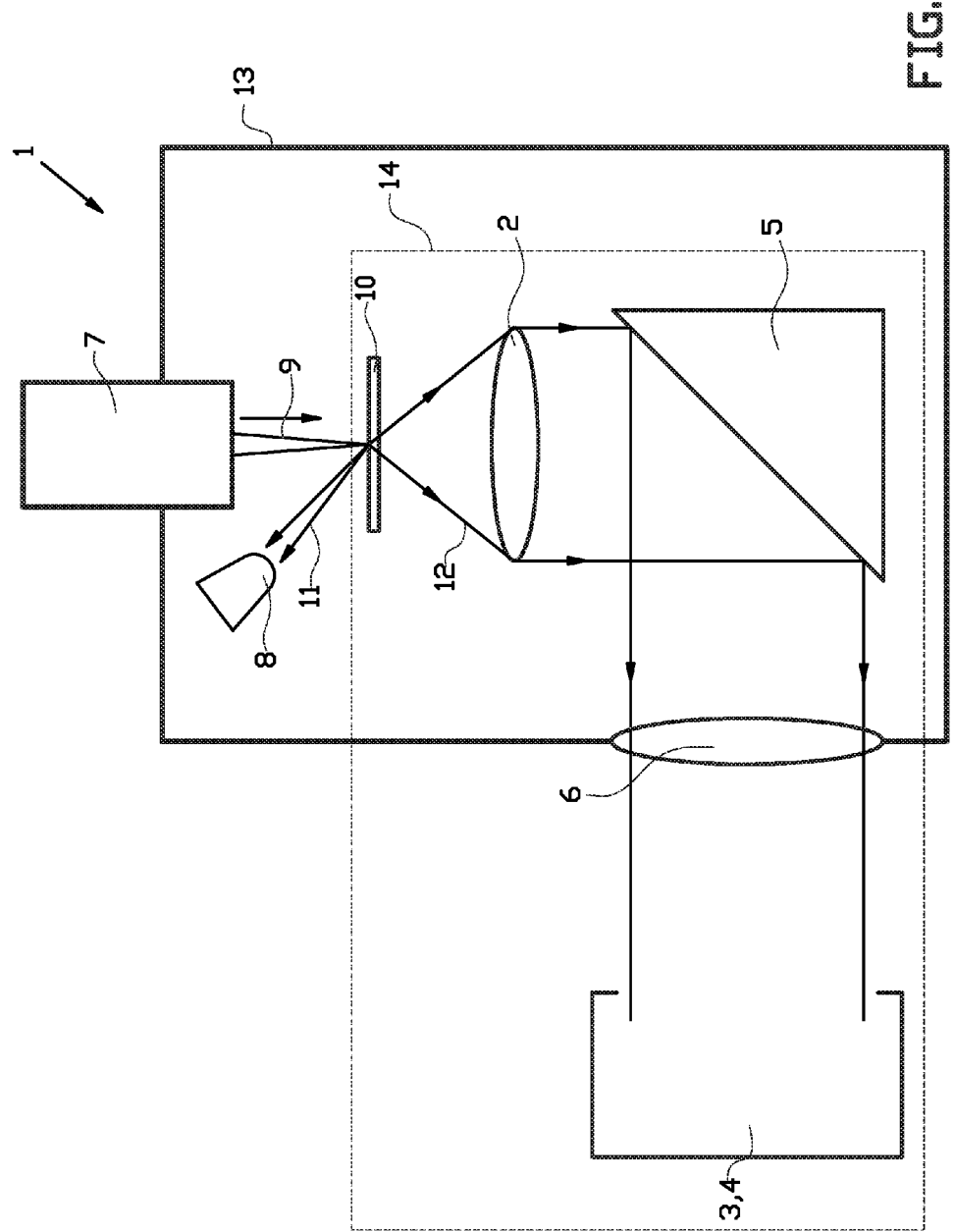
FIG. 2 shows a variation to the basic design of the inspection apparatus of FIG. 1, in which the detection unit of the optical microscope is placed outside the vacuum chamber of the ion- or electron microscope.

FIG. 2 represents an apparatus with the same functionality as the apparatus shown in FIG. 1. The only difference of the apparatus of FIG. 2 in comparison with the apparatus of FIG. 1, is that the photon detector 4 and the pinhole 3 are placed at the outside of the vacuum chamber 13. To this end a mirror 5 within the vacuum chamber 13 is applied to change direction of the luminescence light 12 that comes from the objective 2 and direct it through the optical window 6 towards the pinhole 3 and photon detector 4. Also in this embodiment the closed dashed line 14 encircles the parts of the inspection apparatus 1 of the invention that may all or some of them be mounted on the (replaceable) door of the vacuum chamber 13. These are the same parts as in the embodiment of FIG. 1.

Figure 3:
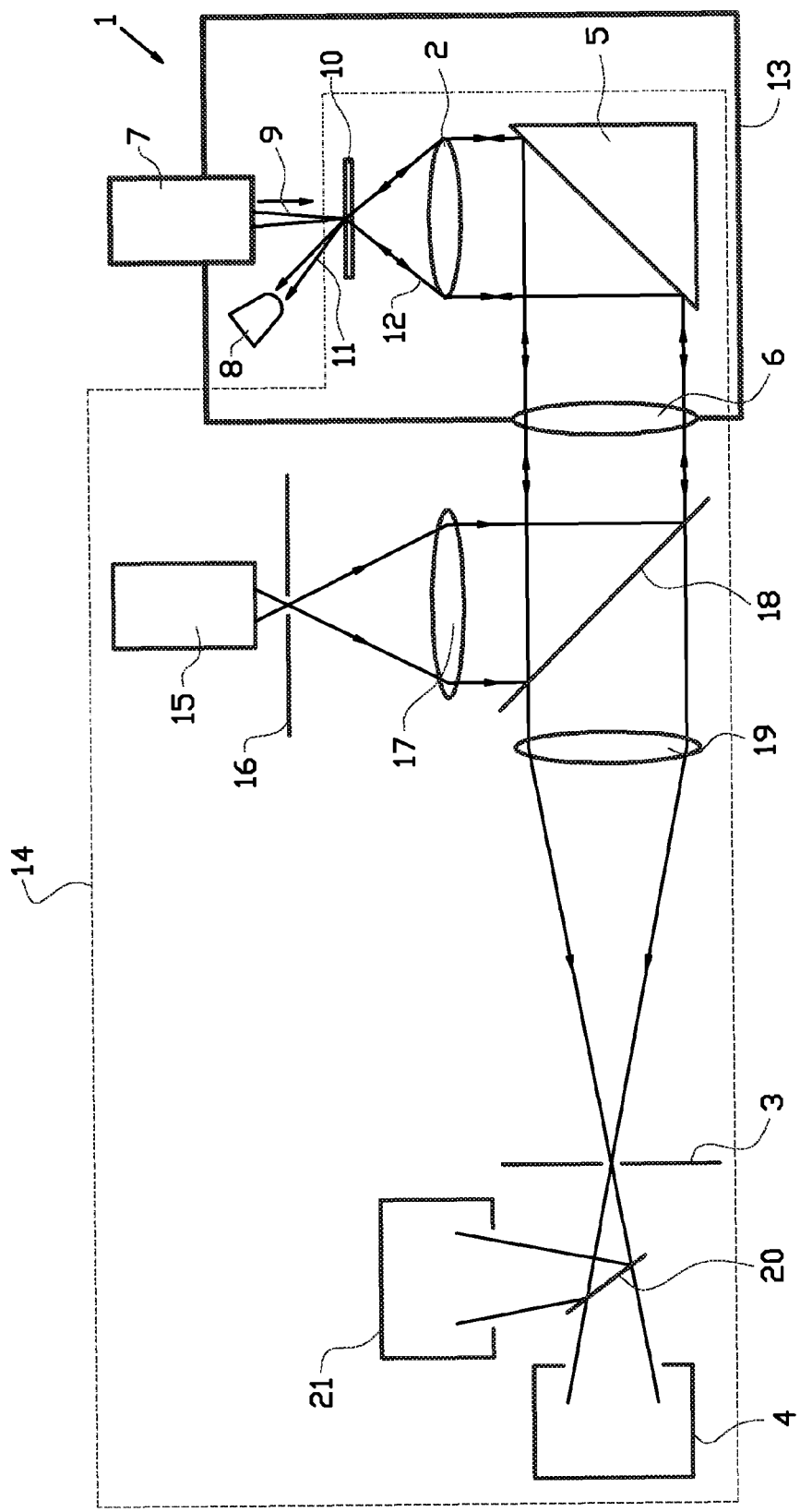
FIG. 3 shows a variation to the design of the inspection apparatus of FIG. 2, completed with a laser excitation and detection unit.

FIG. 3 represents the inspection apparatus 1 of the invention in an embodiment in which is provided with a light source 15 (for instance a laser) and ancillary means for directing light to the sample 10 and excite it to emit luminescence light which is detectable by the optical microscope 2, 3, 4. In the following discussion use will be made of a laser source 15 as a light source, but other light sources may also be applied.

The ancillary means for emitting the light of the laser source 15 to the sample are in the shown embodiment provided by a second pinhole 16, a lens 17 for focusing the laser light via a dichroic mirror 18 through the optical window 6 in the opposite direction of the propagating path of the luminescence light 12 that comes from the sample 10 (as explained with reference to FIG. 2). Upon arriving at the sample 10 this laser light induces further luminescence light from parts of the sample that can be referred to as emitters. When the primary beam 9 of radiation originating from the source 7 of the ion- or electron microscope 7, 8 is scanned through the spot of the sample were said emitters are located, some emitters may switch off (or be modified) due to the action of the primary beam which leads to a modification of the fluorescence signal originating from the sample 10. This modification can be measured and used to trace back the position of those emitters and applied to improve the resolution of the optical microscope to a value in the range of 1 nm similar to the resolution of an ion- or electron microscope. Measurements can be carried out in several manners, for instance by having the primary beam 9 of radiation and the light originating from the light source 15 illuminate the sample 10 simultaneously or with a preselected time-delay.

Similar to the luminescence light 12 that is induced by the primary beam 9 of radiation, the luminescence light that is induced by the light source originating from the light source 15 travels back and exits the vacuum chamber 13 through the optical window 6. After passing the dichroic mirror 18 and the lens 19, the luminescence light passes the pinhole 3 and arrives at the photon-detector 4. Optionally a beam splitter 20 may be applied in combination with a spectrometer 21 for further analysis. Other or multiple detection paths may be also be used.

Likewise as with the previous embodiments, dashed line 14 encircles the parts of the inspection apparatus 1 that are (all or some of them) preferably mounted on the replaceable door of the vacuum chamber 13. In addition to the embodiment of FIG. 2, this also entails the laser source 15 and the ancillary means that are used as explained above for directing light to the sample 10 and excite it to emit luminescence light which is detectable by the optical microscope.

Figure 4:
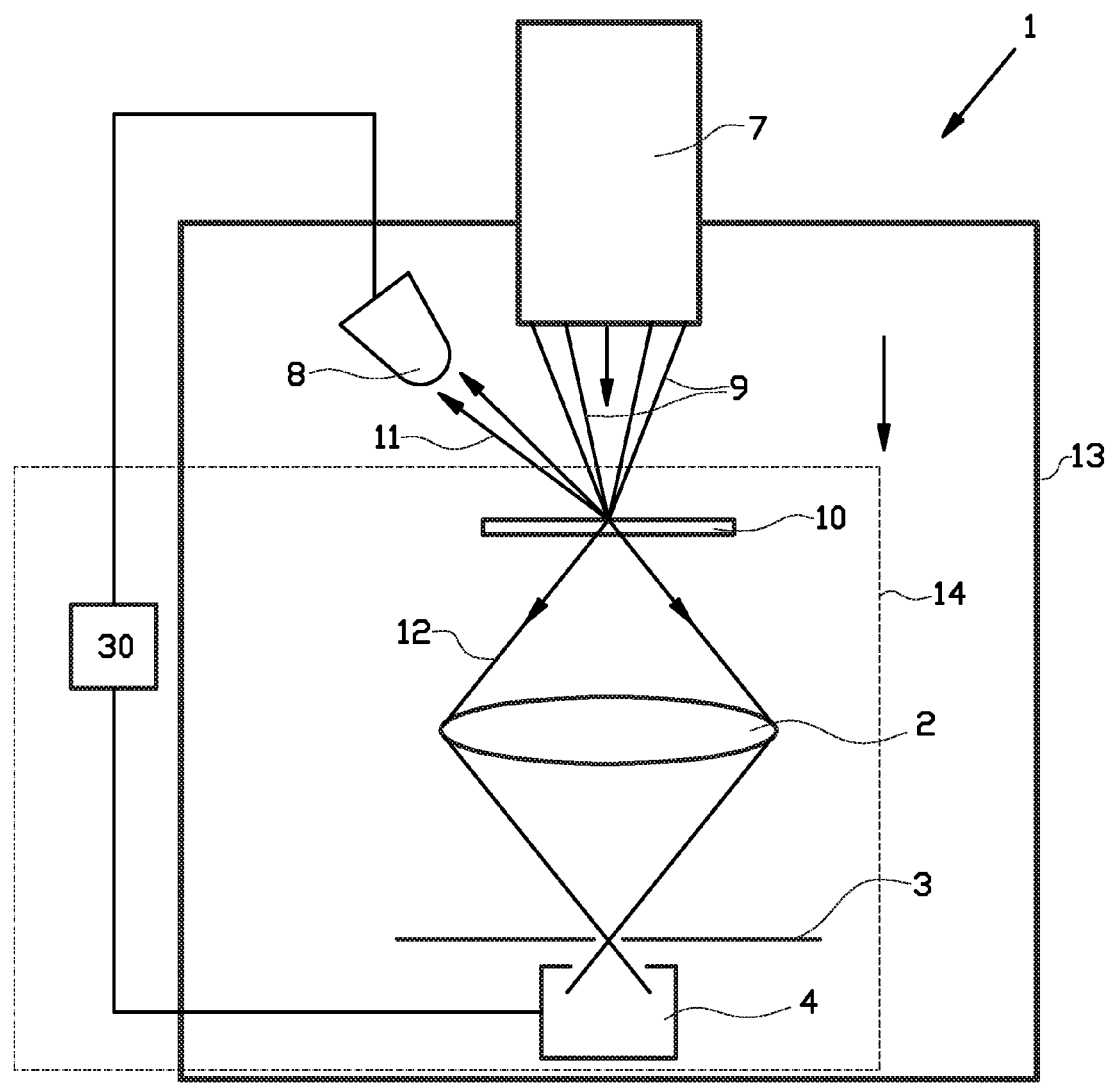
FIG. 4 shows an embodiment of the inspection apparatus of the invention with dual primary beams.

In FIG. 4 a variation to the embodiment shown in FIG. 1 is depicted, in which first of all it is shown that the primary beam 9 of radiation may be directed to the sample at an acute angle with respect to the optical axis of the light collecting device. This can be used to improve resolution but also to apply the apparatus for tomography. Secondly it is shown in FIG. 4 that it is possible to apply two primary beams 9 that are directed at equal angles with respect to the optical axis. When more than two primary beam mare used, they may be directed at equal angles with respect to the optical axis.

The use of multiple primary beams is beneficial for a still further improvement of the resolution, but can also advantageously be used in tomography.

In FIG. 4, a processing unit (30) is provided. A processing unit (30) may also be provided in other embodiments, for example the embodiments of FIGS. 1-3. As described above, the primary beam may influence the luminescence light, emitted by a marker in the sample. It may be the case that the primary beam destroys the marker, thereby preventing the marker from emitting luminescence light. This is generally the case with organic fluorophores or other molecular light emitting markers.

However, a marker may be used that responds differently to the primary beam. For example, markers may comprise semiconductor nanocrystals (SNC), or so-called quantum dots (QD). SNC are tiny inorganic crystalline particles, while most QD are particles containing an inorganic crystalline core surrounded by one or multiple inorganic or organic shells of a different material or composition.

As a consequence of exposure to a primary beam or more in particular an electron beam, an electron may be trapped at the interface of the SNC, leading to a net negative charge at the surface of the SNC. The presence of this charge will change the excited state energy spectrum of the SNC, which can be visualized in the detected signal as a change in emission spectrum, the life time (i.e. the time it takes for a photon to be emitted after illumination by the light or more in particular after an pulse of exciting laser light), or intensity. The presence of the surface charge after electron beam excitation may prevent a charge separation as a consequence of light exciting. This process may cause a momentary variation (for example an increase) in the intensity of the emitted luminescence light.

In the case of QD, an electron may equivalently be trapped at either the outer surface, in one of the shells or in one of the inner interface between core and shell or between different shells. This may cause the same effects as described for SNC.

In an embodiment, the source (7) and the source ancillary means are arranged for emitting said primary beam (9) with a beam intensity to a beam position on said sample during a continuous beam exposure period and for varying the beam intensity during the beam exposure period. The source and ancillary means may comprise switches and/or attenuator for varying the beam intensity. The beam intensity may vary between zero and a maximum intensity or may vary between zero, a maximum intensity and at least one intensity level between zero and the maximum intensity level. The beam intensity may be constant at one of these levels during part of the beam exposure period.

The maximum intensity may be high enough to destroy the emitter or emitting element in the sample. However, in that case the marker may be used only once. Therefore, in a preferred embodiment, the maximum intensity is lower than any intensity that would destroy the emitting element in the sample.

The intensity of the primary beam may be varied with a predefined frequency. In response, the intensity of the received luminescence light may also vary with the same intensity, and thus the signal from the photo-detector may also comprise a signal with this frequency. Therefore, the predefined frequency may be used to filter said signal from the photo-detector. The predefined frequency may be chosen according to the desired measurement and may be larger than, smaller than or about the inverse of the life time of an excitation state of the emitter.

The same may apply to the intensity of the light: In an embodiment, the light source (15) and ancillary means (16, 17, 18, 19, 20, 21) are arranged for directing light with a light intensity to a light position on said sample during a continuous light exposure period and for varying the light intensity during the light exposure period, preferably with a further predefined frequency.

The light intensity may vary between zero and a maximum intensity or may vary between zero, a maximum intensity and at least one intensity level between zero and the maximum intensity level. The light intensity may be constant at one of these levels during part of the light exposure period.

A chopper, an acousto-optic modulator, a blanker, or a pulsed source may be provided for varying the light intensity or the beam intensity with a (further) predefined frequency. The light intensity may also be varied by direction modulation of the light source. The beam intensity may also be varied by a beam blanker.

A signal from the photo-detector may be used or analyzed by a processing unit. The signal may comprise information with respect to the detected luminescence light. Furthermore, a detector may be provided for detecting a secondary radiation (11) backscattered from the sample (10) and induced by the primary beam (9) and/or for radiation emitted, transmitted or scattered from the sample (10) and possibly induced by the primary beam (9).

A signal from the detector may also be sent to the processing unit and the processing unit may use or analyse said signal. This signal may comprise information with respect to the detected radiation.

The processing unit (30) may be provided with a spectrum analyser, an intensity analyser and/or a polarisation analyser in order to analyse the wavelength spectrum, the intensity or the polarisation of the luminescence light respectively.

Based on at least one of these signals and/or analyses, the processing unit may determine characteristics of an element of the sample, wherein the element is an emitting element or an emitter of the luminescence light, for example a marker. The processing unit may determine for example the decay time of an excitation state of the element and may also determine changes in said decay time, indicating a quenching of the life time of an excitation state.

The processing unit may determine changes in the spectrum or polarisation of the emitted luminescence light. This may indicate that a marker is present at the spot of the primary beam on the sample.

In an embodiment, the optical microscope may be provided with two (or more) pinholes between the light collecting device (2) and the photon-detector (4). The pinholes may be arranged next to each other. The photon-detector may be arranged for detecting two beams of luminescence light coming from different location inside the sample, for example fluorescence light from a first location and cathodoluminescence light from a second location. The two light beams may have different wavelengths and may be separated from each other on the basis of their wavelengths. Two pinholes may be provided in order to scan the sample using both light beams simultaneously in a confocal way. The two light beams may be detected by a single photon-detector (for example a CCD camera), having a photon-detecting surface that is large enough to detect the two separate light beams.

The scanning of the sample with the primary beam may take place independently of the scanning of the sample with the light. This is different from the situation wherein an area on the sample is scanned using both the primary beam and the light, before another area is scanned using the primary beam or the light.

As a result of the scanning with the light, areas of interest may be identified. The areas of interest are then scanned with the primary beam, may be in combination with the light. In this way, areas that are of no interest are not scanned with the primary beam. This may increase the speed of scanning the sample. It may also prevent causing damage (by for example radiation) to these non-scanned areas.

In this, scanning may be described as the process of repeatedly (i) exposing a position on the sample during a certain period (for example the light exposure period or the beam exposure period) with the primary beam and/or the light and (ii) exposing another position on the sample during the certain period with the primary beam and/or the light. During the scanning, the photon-detector may detect the luminescence light and provide a signal accordingly. Scanning may performed using an arrangement of predefined scanning positions, for example a raster. However, it may be advantageous to determine or calculate the predefined scanning position on the basis of an image obtained by a previous scan, for example a fluorescence image.

Figure 5:
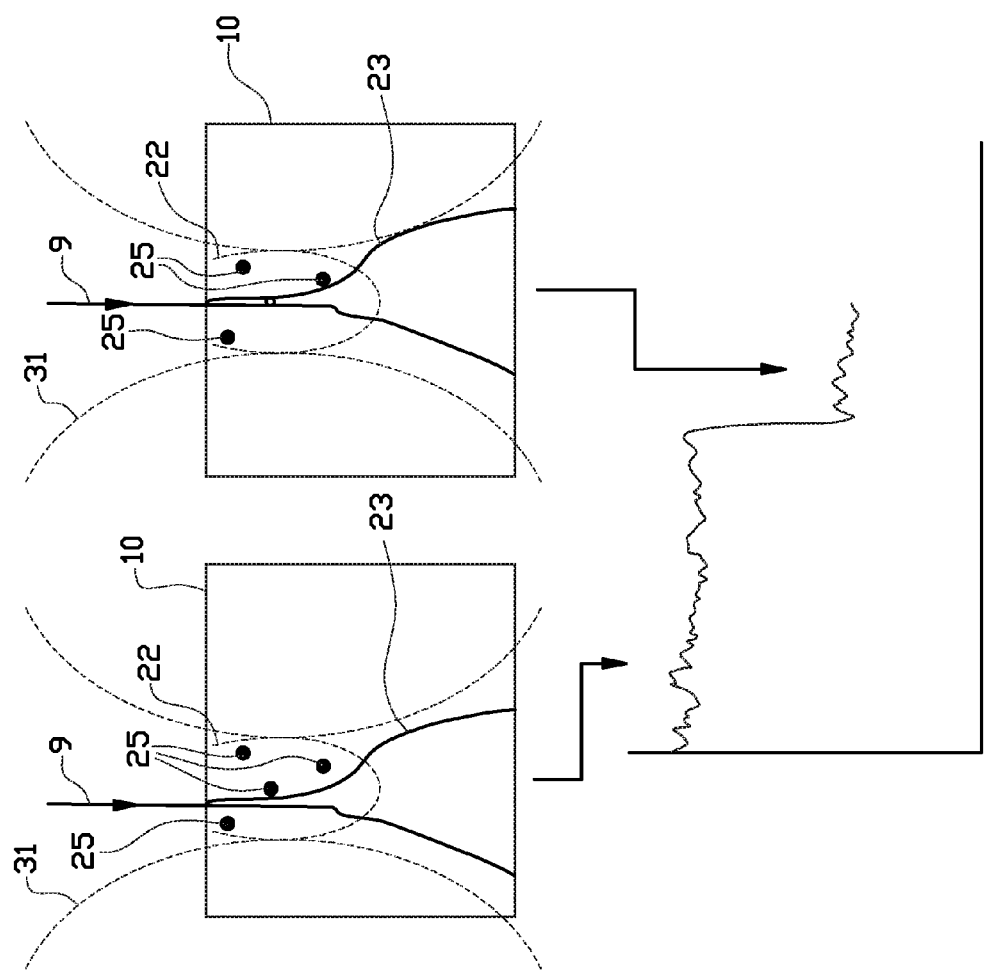
FIG. 5 shows a graph of an intensity of a luminescence light during scanning of a sample and two schematic cross-sections of the sample; and, FIG. 6 shows a schematic cross-section of a sample.
Figure 6:
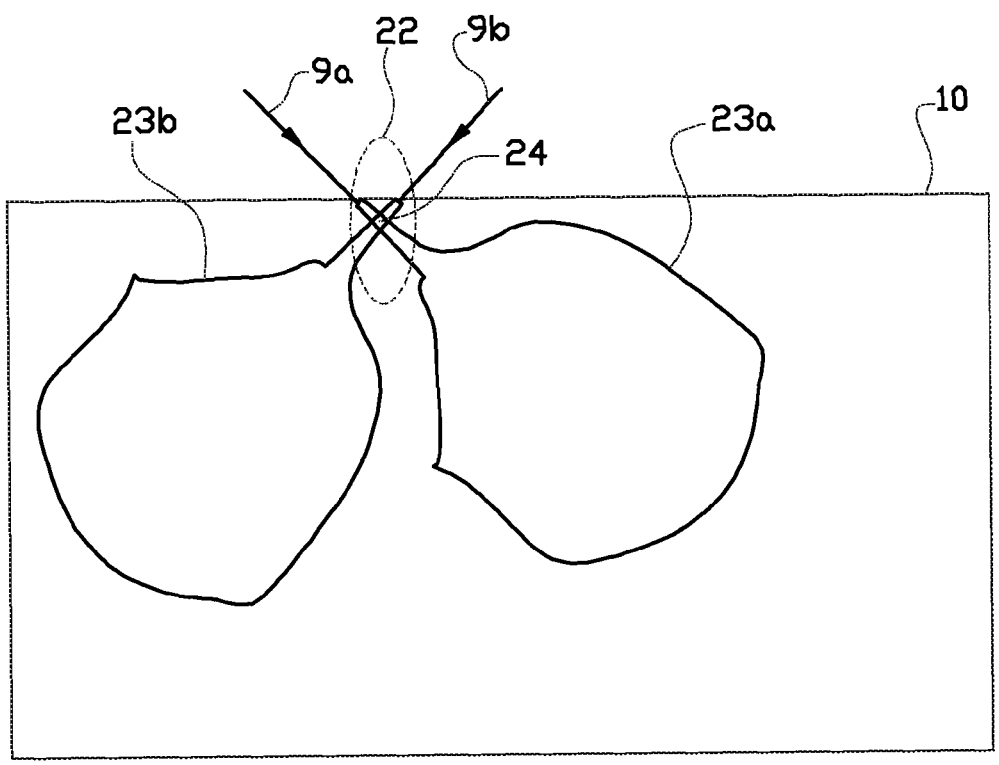

FIGS. 5 and 6 are provided to illustrate the working of the inspection apparatus and the method on a sample according to the invention.

In FIG. 5, a graph of an intensity of a luminescence light during scanning of a sample and two schematic cross-sections of the sample are shown. In the cross-sections, a primary beam (9) is directed at the sample (10). Inside the sample, the primary beam (9) may interact with a volume indicated by 23. Also the sample 10 is illuminated by the light source with a light spot 31 on the sample 10. Because of the use of confocal microscopy only a part of the sample, indicated by 22, is detected. The sample may comprise several markers or fluorescence emitters 25.

When the primary beam is scanned over the sample, the graph of FIG. 5 may be obtained. At the moment of the first cross-section, no markers are located in the overlap volume of 23 and 22 and the detected intensity may be relatively high. At the moment of the second cross-section, one marker is located in the overlap volume of 23 and 22 and this may change the resulting luminescence light, for example its intensity, its wavelength spectrum, its wave vector and/or its time-delay with respect tot the illumination with the light. In the case of FIG. 5, the detected intensity may be relatively low. This variation of intensity may indicate that in the overlap volume a marker is positioned.

Because the overlap volume is smaller than the area 22, a higher resolution or accuracy in determining the position of the marker may be obtained.

It may be understood from FIG. 5, that when the primary beam (9) is directed to the sample at an acute angle with respect to the optical axis of the light collecting device, the overlap volume is further reduced.

Another reduction of the overlap volume and/or an increase in signal-to-noise ratio may be obtained by using two or more primary beams (9a and 9b) as is indicated in FIG. 6. In volume 23a cathodoluminescene light may be generated by primary beam 9a while in volume 23b cathodoluminescene light may be generated by primary beam 9b. Because of the use of confocal microscopy only volume 22 is detected by the optical microscopy.

The presence of markers in the overlap volume 24 will influence the detected luminescence light and in this manner the position of these markers may be detected with a high accuracy.

Embodiments may also be described by the following clauses:

1] Inspection apparatus (1) comprising in combination at least an optical microscope (2, 3, 4) and an ion- or electron microscope (7, 8) equipped with a source (7) for emitting a primary beam (9) of radiation to a sample (10) in a sample holder, and a detector (8) for detection of secondary radiation (11) backscattered from the sample (10) and induced by the primary beam (9), wherein the optical microscope (2, 3, 4) is equipped with a light collecting device (2) to receive in use luminescence light (12) emitted by the sample (10) and induced by the primary beam (9) of radiation and to focus it on a photon-detector (4), characterized in that the optical microscope (2, 3, 4) is of the confocal type having a pinhole (3) between the light collecting device (2) and the photon-detector (4)

2] Inspection apparatus (1) according to clause 1, characterized in that the light collecting device (2) is selected from the group comprising an objective, a mirror, a glassfibre.

3] Inspection apparatus (1) according to clause 1 or 2, characterized in that it is embodied with a light source (15) and ancillary means (16, 17, 18, 19, 20, 21) for directing light to the sample and excite it to emit luminescence light and to enable its detection by the optical microscope (2, 3, 4).

4] Inspection apparatus (1) according to any one of the previous clauses, characterized in that the primary beam (9) of radiation is directed to the sample (10) at an acute angle with respect to the optical axis of the light collecting device (2).

5] Inspection apparatus (1) according to clause 4, characterized in that it has two primary beams (9) that are directed at equal angles of opposite sign to the sample (10)

6] Inspection apparatus (1) according to any one of clauses 1-5, in which the ion- or electron microscope (7, 8) has a vacuum chamber (13) that is provided with a door, characterized in that on the door is mounted one or more selected from the group comprising the sample holder, the optical microscope (2, 3, 4) or a part thereof, the light source (15) and its ancillary means (16, 17, 18, 19, 20, 21) for directing light to the sample.

7] Replaceable door for a vacuum chamber (13) of an ion- or electron microscope (7, 8), characterized in that it is provided with one or more selected from the group comprising a sample holder for a sample (10) to be investigated, an optical microscope (2, 3, 4) of the confocal type or a part thereof, a light source (15) with ancillary means (16, 17, 18, 19, 20, 21) for directing light to a sample (10) to be placed in the sample holder.

8] Method of operating an inspection apparatus (1) comprising in combination at least an optical microscope (2, 3, 4) and an ion- or electron microscope (7, 8) equipped with a source (7) for emitting a primary beam (9) of radiation to a sample (10) in a sample holder, and a detector (8) for detection of secondary radiation (11) backscattered from the sample (10) and induced by the primary beam (9), wherein the optical microscope (2, 3, 4) is equipped with a light collecting device (2) to receive in use luminescence light (12) emitted by the sample (10) and induced by the primary beam (9) of radiation and focus it on a photon-detector (4), wherein the optical microscope (2, 3, 4) is of the confocal type having a pinhole (3) between the light collecting device (2) and the photon-detector (4), and wherein the apparatus is embodied with a light source (15) and ancillary means (16, 17, 18, 19, 20, 21) for directing light to the sample and excite it to emit luminescence light and to enable its detection by the optical microscope (2, 3, 4), characterized in that the primary beam (9) of radiation and the light originating from the light source (15) illuminate the sample (10) simultaneously or with a preselected time-delay.

The invention claimed is:

1. Method of operating an inspection apparatus (1) comprising in combination at least an optical microscope (2, 3, 4) and an ion- or electron microscope (7, 8), comprising the steps of:
   directing light from a light source (15) to the sample (10), the sample comprising at least one emitter, in order to excite the at least one emitter, to emit luminescence light; and,
   directing a primary beam (9), comprising a focused electron or ion beam, to said sample, characterized in that:
modification of the luminescence light (12) as induced by the primary beam (9) is detected.

2. Method according to claim 1, where said modification concerns at least one of:
- the modification of the wavelength spectrum of the luminescence light;
- the intensity of the luminescence light;
- the polarisation of the luminescence light;
- the decay time of an excitation state of the at least one emitter.

3. Method according to claim 1, wherein the primary beam (9) of radiation and the light originating from the light source illuminate the sample (10) with a preselected time-delay.

4. Method according to claim 1, further comprising the step of:
detecting a secondary radiation (11) backscattered from the sample (10) and induced by the primary beam (9) or radiation, emitted, transmitted or scattered from the sample (10).

5. Method according to claim 1, wherein the optical microscope (2, 4) is of the confocal type having a light collecting device (2), a photon-detector (4), and a pinhole (3) between the light collecting device (2) and the photon-detector (4).

6. Method according to claim 1, further comprising the step of:
determining variations, during a light exposure period or a beam exposure period, of at least one of: the detected secondary radiation and detected radiation, emitted, transmitted or scattered from the sample (10).

7. Method according to claim 1, further comprising the step of:
emitting and directing the primary beam (9) to another beam position on said sample after the beam exposure period during another continuous beam exposure period,
wherein the other beam position is located randomly with respect to the beam position; and/or
wherein the other beam position and the beam position are part of a predefined area of interest on said sample.

8. Method according to claim 1, further comprising the step of:
directing the light to another light position on said sample after the light exposure period during another continuous light exposure period,
wherein the other light position is located randomly with respect to the light position; and/or,
wherein the other light position and the light position are part of a predefined area of interest on said sample.

9. Method according to claim 1, further comprising the step of:
emitting and directing the primary beam (9) to another beam position on said sample after the beam exposure period during another continuous beam exposure period; and,
directing the light to another light position on said sample after the light exposure period during another continuous light exposure period;
wherein both said steps take place at the same time, with another time-delay or independently from each other.

10. Inspection apparatus (1) comprising in combination at least an optical microscope (2, 3, 4) and an ion- or electron microscope (7, 8) equipped with a source (7) for emitting a primary beam (9) of radiation, comprising a focused electron or ion beam, to a sample (10) in a sample holder, the sample comprising at least one emitter,
wherein it is embodied with a light source (15) and ancillary means (16, 17, 18, 19, 20, 21) for directing light to the
sample and excite the at least one emitter to emit luminescence light (12) and to enable its detection by the optical microscope (2, 4),
and wherein the optical microscope (2, 3, 4) is equipped with a light collecting device (2) to receive luminescence light (12) emitted by the emitter and to focus it on a photon-detector (4),
wherein modification of luminescence light (12) as induced by the primary beam (9) is detected.

11. Inspection apparatus (1) according claim 10, further comprising a processing unit (30) for analysing a signal from the photo-detector, the signal comprising information with respect to the detected luminescence light,
wherein the processing unit is arranged for analysing at least one of:
- the wavelength spectrum of the luminescence light;
- the intensity of the luminescence light; and,
- the polarisation of the luminescence light.

12. Inspection apparatus (1) according to claim 11, wherein the processing unit (30) is arranged for determining a decay time of an excitation state of the emitter, and/or changes in said decay time, based on said analysing.

13. Inspection apparatus (1) according to claim 10, further comprising a detector (8) for detection of secondary radiation (11) backscattered from the sample (10) and induced by the primary beam (9) or radiation, emitted, transmitted or scattered from the sample (10).

14. Inspection apparatus according to claim 10, wherein the optical microscope (2, 3, 4) is of the confocal type having at least one pinhole (3) between the light collecting device (2) and the photon-detector (4).

15. Inspection apparatus (1) according to claim 10, further comprising the processing unit (30) arranged for determining variations, during the light exposure period or the beam exposure period, of at least one of: the detected secondary radiation and detected radiation, emitted, transmitted or scattered from the sample (10).

16. Inspection apparatus (1) according to claim 10,
wherein the apparatus (1) further comprises source ancillary means, wherein the source (7) and said source ancillary means are arranged for emitting and directing said primary beam (9) with a beam intensity to a beam position on said sample during a continuous beam exposure period and for emitting said primary beam (9) to another beam position on said sample during another continuous beam exposure period after the beam exposure period,
wherein the other beam position is located randomly with respect to the beam position; and/or,
wherein the other beam position and the beam position are part of a predefined area of interest on said sample.

17. Inspection apparatus (1) according to claim 10,
wherein the light source (15) and the ancillary means (16, 17, 18, 19, 20, 21) are arranged for directing light to another light position on said sample during another continuous light exposure period after the continuous light exposure period,
wherein the other light position is located randomly with respect to the light position; and/or
wherein the other light position and the light position are part of a predefined area of interest on said sample.

* * * * *